United States Patent
Boyer et al.

(10) Patent No.: US 7,553,995 B2
(45) Date of Patent: Jun. 30, 2009

(54) METHOD OF PRODUCING TERTIARY AMYL ETHYL ETHER

(75) Inventors: Christopher C. Boyer, Houston, TX (US); Mitchell E. Loescher, Houston, TX (US); Willibrord A. Groten, Houston, TX (US); Mario J. Maraschino, Houston, TX (US); Kerry L. Rock, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 11/853,351

(22) Filed: Sep. 11, 2007

(65) Prior Publication Data
US 2009/0069608 A1  Mar. 12, 2009

(51) Int. Cl.
C07C 43/00 (2006.01)
C07C 41/01 (2006.01)
B01D 3/34 (2006.01)

(52) U.S. Cl. .................. 568/697; 568/579; 203/63; 203/56

(58) Field of Classification Search ........ 568/697, 568/698, 579; 203/56, 63
See application file for complete search history.

(56) References Cited

U.S. PATENT DOCUMENTS

| | | | |
|---|---|---|---|
| 2,480,940 A | 9/1949 | Leum et al. | |
| 2,922,822 A | 1/1960 | Beach | |
| 3,489,243 A | 1/1970 | Prescott et al. | |
| 4,270,929 A | 6/1981 | Dang Vu et al. | |
| 4,302,356 A | 11/1981 | Smith, Jr. | |
| 4,330,679 A | 5/1982 | Kohler et al. | |
| 4,443,559 A | 4/1984 | Smith, Jr. | |
| 4,751,343 A | 6/1988 | Reinhardt et al. | |
| 5,012,031 A | 4/1991 | Schleppinghoff et al. | |
| 5,015,782 A | 5/1991 | Harandi et al. | |
| 5,166,454 A | 11/1992 | Harandi et al. | |
| 5,188,725 A | 2/1993 | Harandi | |
| 5,238,541 A * | 8/1993 | Marquez et al. ........ | 203/56 |
| 5,292,993 A * | 3/1994 | Halsig ................ | 585/864 |
| 5,352,848 A | 10/1994 | Cottrell | |
| 5,414,183 A | 5/1995 | Abrevaya et al. | |
| 5,446,231 A | 8/1995 | Arganbright et al. | |
| 5,453,550 A | 9/1995 | Marquez et al. | |
| 5,489,719 A | 2/1996 | Le et al. | |

(Continued)

OTHER PUBLICATIONS

Kiviranta-Paakkonen, et al., Dehydration of Alcohol in Etherification of Isoamylened with methanol and Ethanol, 1998, Ind. Eng. Chem. Res., vol. 37, pp. 18-24.*

*Primary Examiner*—Porfirio Nazario Gonzalez
*Assistant Examiner*—Yate' K Cutliff
(74) *Attorney, Agent, or Firm*—Osha • Liang LLP

(57) ABSTRACT

A process for the production of tertiary ethers, including: feeding a hydrocarbon stream comprising isoolefins and propionitrile to a distillation column reactor system containing at least one etherification reaction zone; feeding a $C_2$ to $C_6$ monoalcohol or mixture thereof to the distillation column reactor; concurrently in the distillation column reactor system: reacting a portion of the isoolefins with a portion of the alcohols to form a tertiary ether; and separating the tertiary ether from unreacted isoolefins; withdrawing the tertiary ether and propionitrile from the distillation column reactor system as a bottoms; withdrawing the unreacted isoolefins from the distillation column reactor system as an overheads; and operating the distillation column reactor system such that the etherification reaction zone is substantially free of propionitrile.

24 Claims, 4 Drawing Sheets

U.S. PATENT DOCUMENTS

| | | |
|---|---|---|
| 5,491,267 A | 2/1996 | Frey et al. |
| 5,536,886 A | 7/1996 | Tamminen et al. |
| 5,569,790 A | 10/1996 | Frey et al. |
| 5,672,772 A | 9/1997 | Frey et al. |
| 5,675,043 A | 10/1997 | Eppig et al. |
| 5,730,843 A | 3/1998 | Groten et al. |
| 5,847,230 A | 12/1998 | Cottrell et al. |
| 6,019,887 A | 2/2000 | Ramirez de Agudelo et al. |
| 6,037,502 A | 3/2000 | Patton et al. |
| 6,118,037 A | 9/2000 | Piccoli et al. |
| 6,197,163 B1 | 3/2001 | Halsig et al. |
| 6,278,029 B1 | 8/2001 | Forestiere et al. |
| 6,583,325 B1 | 6/2003 | Smith, Jr. et al. |
| 7,025,872 B2 | 4/2006 | Picard et al. |

* cited by examiner

METHOD OF PRODUCING TERTIARY AMYL ETHYL ETHER

BACKGROUND OF DISCLOSURE

1. Field of the Disclosure

Embodiments disclosed herein relate generally to the production of tertiary alkyl ethers. More specifically, embodiments disclosed herein relate to the production of tertiary amyl ethyl ether from feedstocks that contain nitrile impurities, such as acetonitrile and propionitrile.

2. Background

Etherification reactions are the reaction of olefins, such as isobutylene and isoamylenes, or other olefinic compounds, with an alcohol to form the corresponding ether. For example, isobutylene may be reacted with ethanol to form methyl tertiary butyl ether (MTBE).

Etherification reactions may provide for introduction of oxygen into gasoline to produce cleaner burning reformulated fuels. For example, ethers that may be blended with gasoline include MTBE, ethyl tertiary butyl ether (ETBE), tertiary amyl methyl ether (TAME), tertiary amyl ethyl ether (TAEE), and tertiary hexyl methyl ether (THEME), among others. Ethers not only introduce oxygen into gasoline, but they also result in an increased octane rating, may improve the anti-knocking characteristics of the motor fuels, and may reduce the concentration of detrimental components in the exhaust gases.

Etherification reactions may also provide for high purity olefin feedstocks. For example, following etherification of a mixed $C_4$ feedstock to form MTBE, the resulting mixture containing ether may be separated to recover the ether. The MTBE may then be cracked to form alcohol and isobutylene, which may be separated to result in a high purity isobutylene. The resulting high purity isoolefins may be used, for example, in polymerization processes which require a high purity feedstock.

The etherification process typically uses strongly acidic ion exchange resins as etherification catalysts, such as strongly acidic organic polymers. As an isobutylene or isoamylenes molecule meets alcohol at an active catalyst site, the reaction between the olefin and the alcohol takes place, rapidly forming ether.

The activity of the catalyst for etherification reactions is a function of the acid loading or capacity of the resin. This functionality is not linear: a loss of 20% of acid sites on the catalyst results in approximately 50% loss of activity for the conversion to ether. It is therefore important to minimize the deactivation of the catalyst. The loss of catalytic activity may be caused by the adsorption of basic compounds or metal ions, the blockage of the active sites by polymeric products, reaction with acetylenic compounds in the feed, or splitting off the resin's functional groups due to long term operation at temperatures above 240° F. The latter two causes are affected by operating conditions of the etherification reactor. The major source of lost activity is typically from poisons entering with the feedstocks to the unit. Poisons to the catalyst include basic compounds, such as ammonia, amines, caustic soda, and nitrites, for example. In particular, nitriles, such as acetonitrile (ACN) and propionitrile (PN), have been found to deactivate the catalyst. Some studies have shown that nitrites are converted to basic nitrogen compounds which are catalyst poisons, such as described in U.S. Pat. No. 5,675,043. Regardless of the actual poison, nitrites or derivatives thereof are generally not desired to be fed to the etherification reaction vessel due to the potential for catalyst deactivation.

In refinery applications, the largest source of hydrocarbon feedstock containing isoolefins is the stream from the fluidized catalytic cracking unit (FCCU). Some $C_4$s and $C_5$s are also obtained from fluid or delayed cokers. Nitriles formed in these units enter the etherification process with the hydrocarbon feed stream. The amount of nitriles in the feed varies with the severity of the catalytic cracker operation, crude source, and catalyst used in the FCCU.

Propionitrile has been found to be a particular problem in the $C_5$ stream. Unlike other feed poisons which may deactivate the catalyst in a plug flow fashion through the catalyst bed, nitriles' deactivation mechanism is not immediate. Rather, it results in a diffused deactivation throughout the entire bed. In order to obtain adequate run lengths with the catalyst, it is important to minimize the contact of the catalyst with poisons, including nitrites.

Etherification processes include fixed bed reaction systems, catalytic distillation systems, and combinations of fixed bed reactors and catalytic distillation, among others. Such processes are described in U.S. Pat. Nos. 5,238,541, 5,489,719, 5,491,267, 6,037,502, 5,446,231, 5,536,886, 6,583,325, 5,166,454, and 5,188,725, among others.

Many of the above listed patents describing etherification processes recognize the need to minimize contact between etherification catalysts and nitrites. Several processes have been proposed to remove nitrites from the etherification unit feed. For example, U.S. Pat. Nos. 5,569,790, 5,672,772, 5,847,230, 6,037,502, 6,118,037, 6,278,029 disclose etherification processes in which the nitrites are removed from $C_4$ and $C_5$ hydrocarbon streams by washing the hydrocarbon stream with water and/or alcohols to extract the nitrites into the water phase. However, as noted in U.S. Pat. Nos. 5,446,231 and 6,019,887, water washing may be inefficient at extracting nitrites, especially propionitrile.

Other processes to protect etherification catalysts from deactivation with nitrites include solvent extraction, selective hydrogenation of dienes, hydrolysis, hydrogenation of nitrogen and sulfur containing compounds, reactive guard beds, nitrogen removal units, and adsorption, each prior to etherification. Other processes include integrating catalysts for use in FCC and etherification processes, or using other processes which provide for catalyst beds that may be regenerated, such as esterification, followed by subsequent reaction stages. Examples of these processes may be found in, for example, U.S. Pat. Nos. 5,015,782, 5,166,454, 5,188,725, 5,352,848, 5,414,183, 5,491,267, 6,019,887, 6,118,037, and 7,025,872. With regard to guard beds, however, as noted in U.S. Pat. Nos. 5,292,993 and 6,197,163, catalyst poison removal may be inefficient, or some catalyst poisons may be able to pass through a conventional guard bed.

Another process to protect etherification catalysts from deactivation with nitrites includes the azeotropic distillation of the reactants, hydrocarbons and alcohols, prior to the etherification reactor. For example, methanol azeotropic distillation is described in U.S. Pat. Nos. 5,238,541, 5,292,993, 5,453,550, 5,446,231, and 6,197,163. For example, in U.S. Pat. No. 5,238,541, the hydrocarbon stream containing isoolefins is contacted with alcohol and the mixture is distilled. As a result of the azeotropes formed in the mixture, the hydrocarbons may be removed overhead with some alcohol while the nitrites, alcohol, and heavier hydrocarbons are removed in the bottoms, resulting in a hydrocarbon feedstock, taken as overheads, substantially free of nitrites. The alcohol/hydrocarbon mixture may then be used as a direct feed to the etherification unit as alcohol is a reactant in the process.

In U.S. Pat. No. 5,446,231 ('231), incorporated herein by reference, a hydrocarbon stream containing nitrites is contacted with a methanol-water mixture to extract the nitrites. The resulting water-methanol-nitriles mixture is then distilled to recover water as a bottoms and nitrile-contaminated methanol as overheads. The hydrocarbons, having decreased nitrile content, may then be fed to an etherification reactor.

In one embodiment of '231, the methanol-nitrile mixture is fed to a catalytic distillation reactor at a point below the catalyst zone. The methanol forms an azeotrope with the hydrocarbons and is distilled into the catalyst zone. The nitriles do not enter the methanol-hydrocarbon azeotrope and remain in the ether product, collected as the bottoms from the catalytic distillation reactor. The net effect is to hold the nitrites out of contact with the cation resin catalyst and to return them to the stream following conversion to the higher octane ether, thus extending catalyst life.

In a separate embodiment, '231 discloses that ethanol-water blends may be used effectively for the extraction of propionitrile from a $C_5$ fraction. '231 further teaches that the propionitrile must be removed from the ethanol prior to recycle to the catalytic reactor in order to protect the catalyst. With use of ethanol-water mixtures, '231 indicates that hydrogenation of the nitrites to amines would be appropriate. Thus, while nitrile-contaminated methanol may be fed to the distillation column reactor, '231 indicates that nitrile-contaminated ethanol should not be fed to the distillation column reactor.

In general, as discussed above, these and other references teach that it is undesirable to feed nitrites to the etherification reaction vessel due to heightened potential for catalyst deactivation. To prevent catalyst deactivation due to nitrites, many of the above described processes may include a significant number of reactors and separators (a high piece count), translating to higher capital costs, increased complexity to the overall process, and increased operating costs (energy, raw materials, purification); may result in decreased olefin feed concentration; and/or, as described above, may be inefficient at deactivating contaminant/propionitrile removal.

Accordingly, there exists a need for a process to produce ethers from $C_4$ to $C_6$ hydrocarbon streams, where the process may have a reduced piece count, may effectively avoid deactivation of the etherification catalysts, and/or may provide an economic alternative to prior art etherification processes.

SUMMARY OF THE DISCLOSURE

In one aspect, embodiments disclosed herein relate to a process for the production of tertiary ethers. The process may include: feeding a hydrocarbon stream comprising isoolefins and propionitrile to a distillation column reactor system containing at least one etherification reaction zone; feeding a $C_2$ to $C_6$ monoalcohol or mixture thereof to the distillation column reactor; concurrently in the distillation column reactor system: reacting a portion of the isoolefins with a portion of the alcohols to form a tertiary ether; and separating the tertiary ether from unreacted isoolefins; withdrawing the tertiary ether and propionitrile from the distillation column reactor system as a bottoms; withdrawing the unreacted isoolefins from the distillation column reactor system as an overheads; and operating the distillation column reactor system such that the etherification reaction zone is substantially free of propionitrile.

In another aspect, embodiments disclosed herein relate to a process for the production of tertiary amyl ethyl ether. The process may include: feeding a hydrocarbon stream comprising $C_5$ isoolefins and propionitrile to a distillation column reactor containing at least one etherification distillation reaction zone, wherein the stream comprising the hydrocarbons is fed to the distillation column reactor at a point below the etherification distillation reaction zone; feeding ethanol to the distillation column reactor; concurrently in the distillation column reactor: reacting a portion of the $C_5$ isoolefins with a portion of the ethanol to form tertiary amyl ethyl ether; and separating the tertiary amyl ethyl ether from unreacted $C_5$ isoolefins; withdrawing the tertiary amyl ethyl ether and propionitrile from the distillation column reactor as a bottoms; withdrawing the unreacted $C_5$ isoolefins from the distillation column reactor as an overheads; and operating the distillation column reactor such that the etherification distillation reaction zone is substantially free of propionitrile.

Other aspects and advantages will be apparent from the following description and the appended claims.

DETAILED DESCRIPTION

Figure 1:
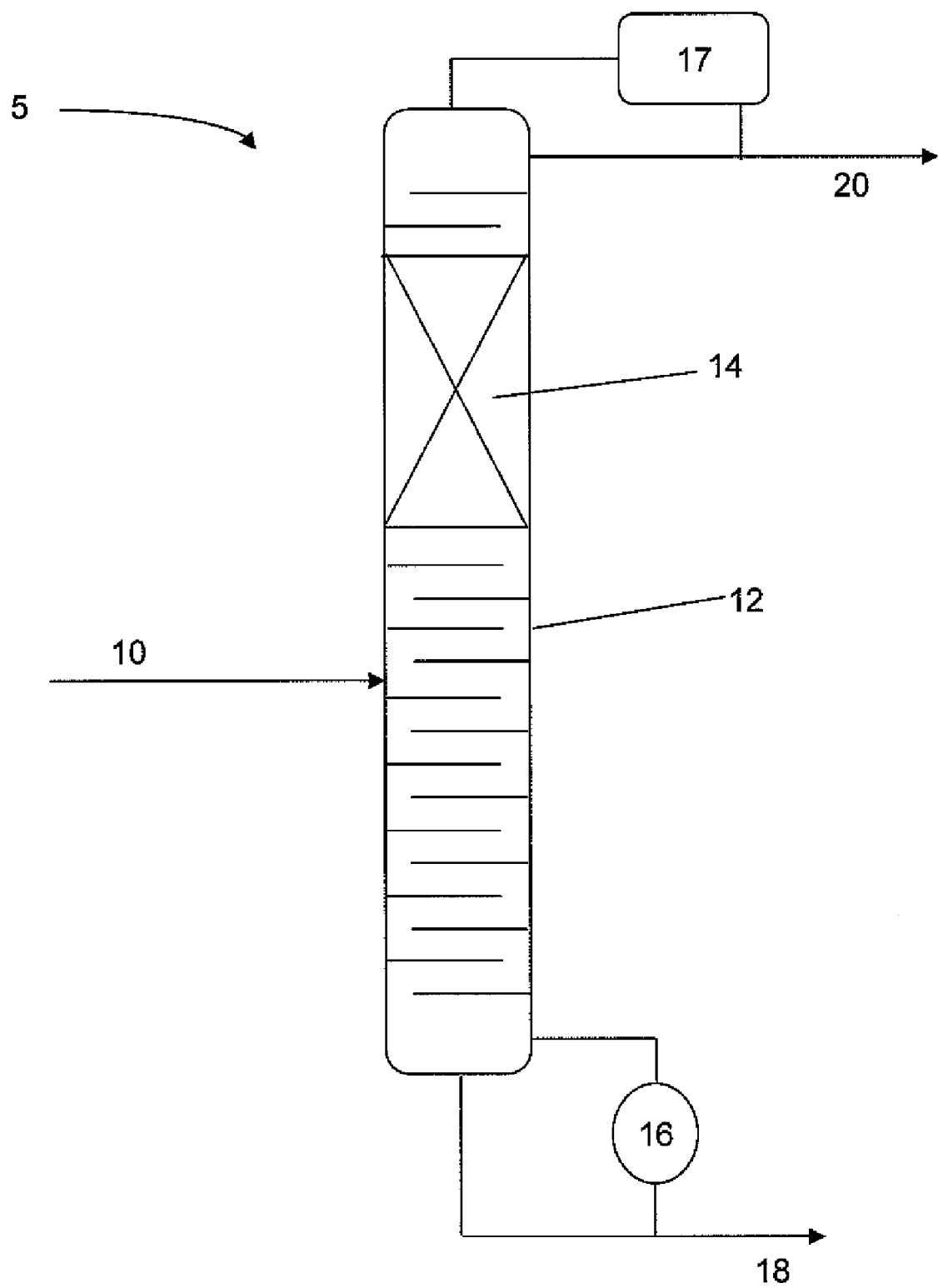
FIG. 1 is a simplified flow diagram of a catalytic distillation reactor system according to embodiments disclosed herein.

In one aspect, embodiments disclosed herein relate to an etherification process wherein a feedstock containing hydrocarbons, in particular $C_4$ to $C_7$ hydrocarbons, is fed into a catalytic distillation reactor system. $C_4$ to $C_6$ isoolefins contained in the feedstock are reacted with an alkanol in the presence of a cation exchange resin to form tertiary alkyl ethers.

In a more specific aspect, embodiments disclosed herein relate to an etherification process, wherein a feedstock containing hydrocarbons and nitriles, including propionitrile, is fed into a catalytic distillation reactor system along with $C_2$ to $C_6$ alcohols. The etherification process may be operated in a manner such that essentially all of the propionitrile does not come into contact with the etherification catalyst.

Applicant has surprisingly found that, contrary to the teachings of the prior art, etherification process conditions may be selected that provide for effective etherification of $C_4$ to $C_6$ isoolefins with ethanol or higher alcohols, and limited or negligible catalyst deactivation due to nitrites. Embodiments of the etherification processes described herein may provide for one or more of extended catalyst life, process flexibility, and reduced piece count, which may result in decreased capital costs, a less complicated reaction system, and decreased operating costs, among other benefits.

Within the scope of this application, the expression "catalytic distillation reactor system" denotes an apparatus in which the etherification reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

As described above, embodiments disclosed herein relate to etherification of olefinic hydrocarbons by reacting olefins with an alcohol using an etherification catalyst. Each of these components is described in more detail below, followed by a description of embodiments of the etherification process disclosed herein.

Hydrocarbon Feed

Hydrocarbon feedstocks for use in embodiments of the etherification process described herein may include $C_3$ to $C_9$ and higher hydrocarbons. For example, refinery streams are usually separated by fractional distillation. A light naphtha cut is one such refinery stream and because they often contain compounds that are very close in boiling points, the separations are not precise. Thus, a $C_5$ stream, for instance, may include $C_4$s and up to $C_8$s and higher. These components may be saturated (alkanes), unsaturated (mono-olefins), and poly-unsaturated (diolefins, for example). Additionally, the components may be any or all of the various isomers of the individual compounds. Such a mixture may easily contain 150 to 200 components, including the nitrile contaminants. Other hydrocarbon streams of $C_4$ to $C_9$ carbon atoms may be used in embodiments disclosed herein.

In some embodiments, hydrocarbon feedstocks may include a $C_4$ cut, which may include $C_3$ to $C_5$ or higher hydrocarbons (i.e., $C_{6+}$), including olefins and the nitrile contaminants. In other embodiments, hydrocarbon feedstocks may include a $C_5$ cut, which may include $C_4$ to $C_8$ or higher hydrocarbons, including olefins and the nitrile contaminants. In other embodiments, hydrocarbon feedstocks may include a $C_6$ cut, which may include $C_4$ to $C_9$ or higher hydrocarbons, including olefins and the nitrile contaminants. In other various embodiments, hydrocarbon feedstocks may include mixtures of one or more of $C_4$, $C_5$, $C_6$, and $C_{7+}$ hydrocarbons, where the mixture includes olefinic compounds and nitrile contaminants. The above described streams may include $C_4$ to $C_7$ streams, gasoline fractions, FCC gasoline, coker gasoline, and other refinery streams having similar properties.

Saturated compounds included in the above described hydrocarbon streams may include various isomers of butane, various isomers of pentane, and various isomers of hexane, among others, for example. Olefinic compounds included in the above described hydrocarbon streams may include isobutylene, various isomers of pentene, and various isomers of hexene, among others, for example. In some embodiments, the hydrocarbon streams may be derived from any source, and may include a concentration of 1 to 35 weight percent etherifiable isoolefins; a concentration of 10 to 30 weight percent isoolefins in other embodiments; and a concentration of 15 to 25 weight percent isoolefins in yet other embodiments.

Other embodiments disclosed herein are broadly applicable to the production of a wide variety of ethers from a number of different feedstocks. The primary ethers resulting in processes disclosed herein may include tertiary-amyl, tertiary-butyl, and tertiary-hexyl ethers. Where the etherification process is one for the production of butyl ethers, the typical feed stream will consist of a mixture of $C_4$ isomers comprising isobutane, isobutylene, normal butane, 1-butene and 2-butene. Where the process is one for the production of amyl ethers, the feed stream components will include 3-methyl-1-butene, isopentane, 1-pentene, 2-methyl-1-butene, normal pentane, trans-2-pentene, cis-2-pentene and 2-methyl-2-butene in a typical distribution of isomers. Although a variety of sources are available to provide such hydrocarbon feed streams, the most common sources for the feed streams for these processes are light cracked hydrocarbon streams from an FCC unit or a $C_4$ stream from a steam cracker after butadiene extraction. In one embodiment, the etherification feedstream of the present invention comprises isoamylene, which may include both the reactive isomers (2-methyl-1-butene and 2-methyl-2-butene) and unreactive isomer (3-methyl-1-butene).

Hydrocarbon streams used in some embodiments may include propionitrile at a concentration of 1 ppm or greater. In other embodiments, hydrocarbon streams may include propionitrile at a concentration of 2 ppm or greater; 5 ppm or greater in other embodiments; 10 ppm or greater in yet other embodiments; 20 ppm or greater in other embodiments; and 50 ppm or greater in yet other embodiments.

Alcohols

Alcohols useful in embodiments disclosed herein may include $C_2$ to $C_6$ primary and secondary alcohols. The term "alcohol" includes lower alkyl alcohols capable of forming azeotropes with the saturated and unsaturated hydrocarbons, in particular the $C_3$ to $C_7$ hydrocarbons, of the hydrocarbon feedstock. Examples of alcohols useful in embodiments disclosed herein include ethanol, n-propanol, i-propanol, n-butanol, i-butanol and t-butanol. In some embodiments, methanol may be used in combination with one or more of the $C_{2+}$ alcohols.

Catalyst

Any catalyst typically used in etherification processes may be used in embodiments disclosed herein. Conventional cation exchange resins and/or zeolites may be used in various embodiments. Thus, the resin may contain sulfonic acid groups and may be obtained by polymerization or copolymerization of aromatic vinyl compounds followed by sulfonation. Examples of aromatic vinyl compounds suitable for preparing polymers of copolymers include: styrene, vinyl toluene, vinyl naphthalene, vinyl ethyl-benzene, methyl styrene, vinyl chlorobenzene and vinyl xylene. The acid cation exchange resin may contain some 1.3 to 1.9 sulfonic acid groups per aromatic nucleus. In some embodiments, resins may be based on copolymers of aromatic monovinyl compounds with aromatic polyvinyl compounds in which the polyvinyl benzene content is from about 1 to 20 weight percent of the copolymer. The ion exchange resin may have a granular size of about 0.15 to 1 mm in some embodiments. In addition to the above resins, perfluorosulfonic acid resins, which are copolymers of sulfonyl fluorovinyl ethyl and fluorocarbon, may be used.

The catalysts useful in the etherification processes disclosed herein may contain a zeolite sometimes referred to as medium pore or ZSM-5 type. In other embodiments, the zeolite may be a medium pore shape selective acidic metallosilicate zeolite selected from the group consisting of ZSM-5, ZSM-11, ZSM-12, ZSM-22, ZSM-23, ZSM-35, ZSM-50, MCM-22, as well as larger pore zeolite Y and zeolite Beta. The original cations associated with zeolites utilized herein may be replaced by a wide variety of other cations according to techniques well known in the art, e.g., by ion exchange. Typical replacing cations include hydrogen, ammonium, alkyl ammonium, and metal cations, and their mixtures. In the case of metal cations, metals of Groups IB to VIIIA of the Periodic Table, including, by way of example, iron, nickel cobalt, copper, zinc, palladium, calcium, chromium, tungsten, molybdenum, rare earth metals, etc. may be used. These metals may also be present in the form of their oxides.

In other embodiments, etherification catalysts for the isoalkene reactants include mineral acids such as sulfuric acid, boron trifluoride, phosphoric acid on kieselguhr, phosphorous-modified zeolites, heteropoly acids, and various sulfonated resins. These resin type catalysts may include the reaction products of phenolformaldehyde resins and sulfuric acid and sulfonated polystyrene resins including those crosslinked with divinylbenzene. A particular etherification catalyst is a macroporous acid-form of a sulfonic ion exchange resin such as a sulfonated styrene-divinylbenzene resin, as described in U.S. Pat. No. 2,922,822, having a degree of crosslinking of about 5 to 60%. Specialized resins have been described in the art and include copolymers of sulfonyl fluorovinyl ether and fluorocarbons, as described in U.S. Pat. No. 3,489,243. Another specially prepared resin consists of $SiO_2$-modified cation exchangers described in U.S. Pat. No. 4,751,343. The macroporous structure of a suitable resin is described in detail in U.S. Pat. No. 5,012,031 as having a surface area of at least about 400 $m^2$/g, a pore volume of about 0.6 to 2.5 ml/g, and a mean pore diameter of 40 to 1000 Angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929.

In some embodiments, a catalytic distillation structure for use herein includes placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction, such as cotton, linen, fiber glass cloth, or TEFLON. U.S. Pat. Nos. 4,302,356, 4,443,559, and 5,730,843 disclose catalyst structures which are useful as distillation structures, and are incorporated herein by reference.

Etherification Reactions

As described above, isoolefins and alcohols may be reacted to form ethers. Examples of ethers formed in embodiments disclosed herein may include: ethyl tertiary butyl alcohol (ETBE), the reaction product of isobutylene and ethanol; tertiary amyl ethyl ether (TAEE), the reaction product of isoamylenes and ethanol; tertiary hexyl ethyl ether (THEE), the reaction product of various $C_6$ isoolefins with ethanol; as well as the propyl, butyl, amyl, and hexyl counterparts resulting from the reaction of the isoolefin with $C_3$ to $C_6$ alcohols. In some embodiments, such as where a mixture of alcohols including methanol is used, ethers produced may include the methyl ethers formed by reaction of the isoolefins with methanol.

Distillation Column Reactor Systems

Figure 2:
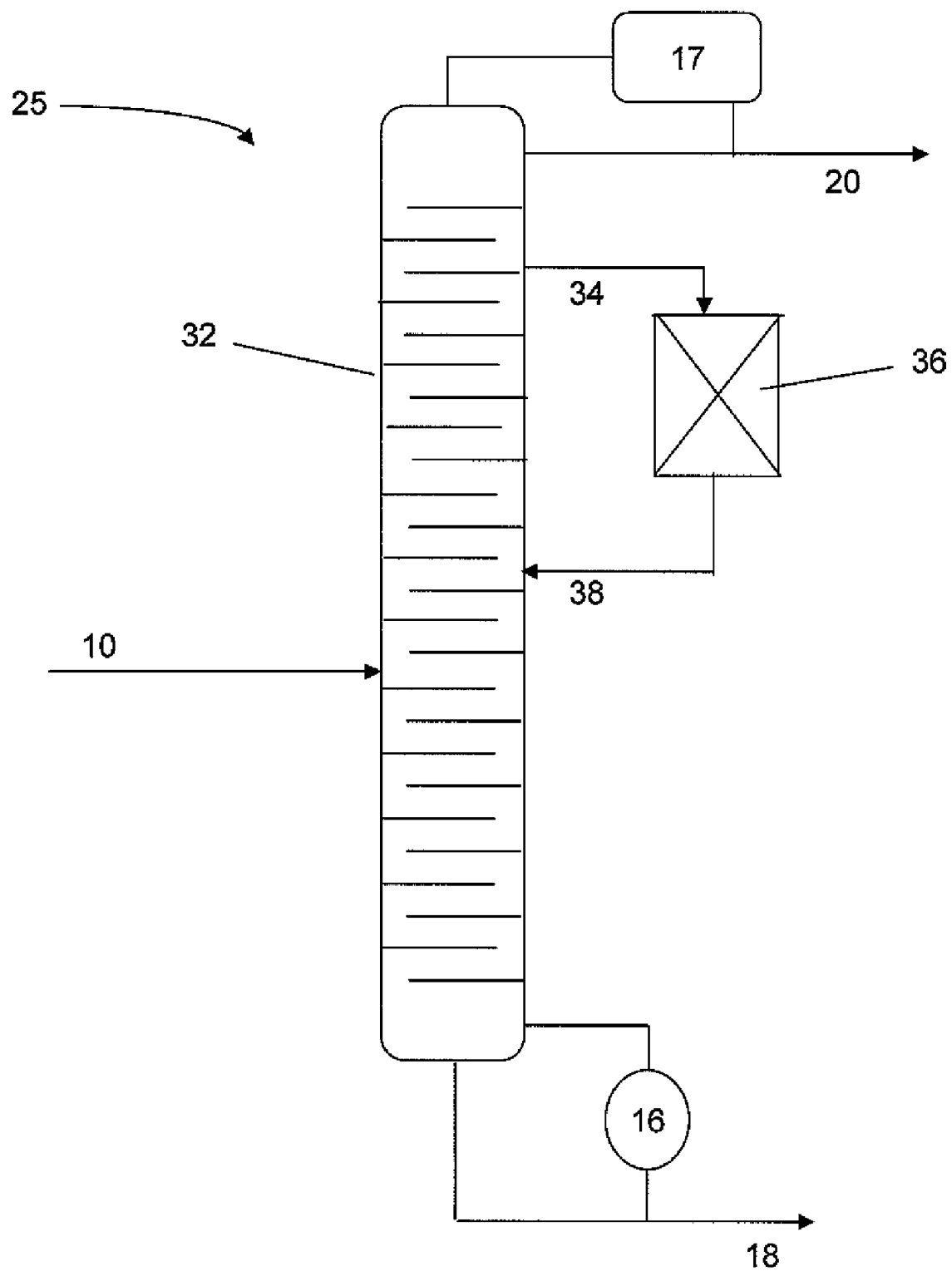
FIG. 2 is a simplified flow diagram of a catalytic distillation reactor system according to embodiments disclosed herein.

Distillation column reactor systems useful in embodiments disclosed herein are illustrated in FIG. 1 and FIG. 2. One skilled in the art would recognize that valves, pumps, utilities, and other items necessary for operation are omitted for purposes of simplifying the flow diagrams presented.

Referring initially to FIG. 1, a distillation column reactor system 5 according to some embodiments disclosed herein is illustrated. Hydrocarbon stream 10 containing nitrites may be fed to a distillation column reactor 12. The feed location of hydrocarbon stream 10 may be at any stage below a catalyst containing region 14. Isoolefins contained in hydrocarbon stream 10 may react with alcohols in catalyst containing region 14 to produce ethers. Distillation column reactor 12 may include a reboiler 16 and an overhead system 17, each providing for control of the liquid and vapor traffic in distillation column reactor 12.

Distillation column reactor system 5 may be operated in a manner such that nitrites contained in hydrocarbon stream 10 exit distillation column reactor 12, along with heavier hydrocarbons contained in hydrocarbon stream 10 and the ethers formed due to reaction of the olefins and the alcohols, in bottoms stream 18. Light hydrocarbons, including alkanes and unreacted olefins may be condensed in the overhead system 17 and recovered in overheads stream 20 or recycled as reflux to the top of distillation column reactor 12.

Alcohols may be fed to distillation column reactor 12 along with hydrocarbon stream 10, or may be fed separately (not shown) to a different location on distillation column reactor 12, including stages above or below the feed point of hydrocarbon feed stream 10. Due to azeotropes that may form between the alcohols and the various hydrocarbons and ethers, as well as the selected operating conditions, alcohols may be present in both bottoms stream 18 and overheads stream 20.

Referring now to FIG. 2, a distillation column reactor system 25 according to other embodiments is illustrated, where like components are indicated by like numerals. Hydrocarbon stream 10 containing nitrites may be fed to a distillation column 32. A reboiler 16 may be in fluid communication with the bottom of distillation column 32, and overhead system 17 may be in fluid communication with the top of distillation column 32, where each may provide for control of the vapor and liquid traffic within distillation column 32. Distillation column 32 may include valve trays, sieve trays, bubble-cap trays, packing, structured packing, random packing, or other structures known to those skilled in the art for performing distillations.

A liquid draw 34 may be withdrawn from the column at a stage above the feed location of hydrocarbon stream 10. Liquid draw 34, containing olefins and alcohols, may then be fed to an etherification reactor 36, containing etherification catalyst, to produce ethers. The ethers, inert compounds, and unreacted alcohols and olefins may be recovered in mixed product stream 38, which may then be fed back to distillation column 32 at a point below the location of liquid draw 34.

Distillation column reactor system 25 may be operated in a manner such that nitrites contained in hydrocarbon stream 10 exits distillation column 32, along with heavier hydrocarbons contained in hydrocarbon stream 10 and the ethers formed due to reaction of the olefins and the alcohols, in bottoms stream 18. Light hydrocarbons, including alkanes and unreacted olefins may be condensed in the overhead system 17 and recovered in overheads stream 20.

Alcohols may be fed to distillation column 32 along with hydrocarbon stream 10, or may be fed to a different location on distillation column 32, including stages above or below the feed point of hydrocarbon feed stream 10. Due to azeotropes that may form between the alcohols and the various hydrocarbons, as well as the selected operating conditions, alcohols may be present in both bottoms stream 18 and overheads stream 20.

In a more specific embodiment, the above described distillation column reactor systems may be used to produce tertiary amyl ethers. Referring again to FIG. 1, a hydrocarbon stream 10 containing a $C_5$ cut and nitrites may be fed to a distillation column reactor 12. As described above, the $C_5$ cut may include isomers of pentane and isomers of pentenes, including reactive and non-reactive isomers. The feed location of hydrocarbon stream 10 may be at any stage below a catalyst containing region 14. Isoolefins contained in hydrocarbon stream 10 may react with ethanol in catalyst containing region 14 to produce tertiary amyl ethyl ethers. Distillation column reactor 12 may include a reboiler 16 and an overhead system 17, each providing for control of the liquid and vapor traffic in distillation column reactor 12.

Distillation column reactor system 5 may be operated in a manner such that nitrites contained in hydrocarbon stream 10 exit distillation column reactor 12, along with any heavier hydrocarbons contained in the $C_5$ cut hydrocarbon stream 10 and the ethers formed due to reaction of the olefins and the alcohols, in bottoms stream 18. Light hydrocarbons, including any lighter alkanes and unreacted olefins contained in the $C_5$ cut may be condensed in the overheads system 16 and recovered in overheads stream 20 or recycled as reflux to the top of distillation column reactor 12.

Ethanol may be fed to distillation column reactor 12 along with hydrocarbon stream 10, or may be fed to a different location on distillation column reactor 12, including stages above or below the feed point of hydrocarbon feed stream 10. Due to azeotropes that may form between ethanol and the various hydrocarbons, as well as the selected operating conditions, ethanol may be present in both bottoms stream 18 and overheads stream 20.

Similarly, distillation column reactor system 25, illustrated in FIG. 2, may also be used to produce tertiary amyl ethyl ethers. Similar descriptions may also be given for specific $C_4$ and $C_6$ cuts, or for various mixtures of hydrocarbons, including mixtures of $C_4$s and $C_5$s, mixtures of $C_5$s and $C_6$s, and mixtures of $C_4$s to $C_7$s and mixtures of $C_5$s to $C_7$s, to name a few.

Operation of the Distillation Column Reactor Systems

As described above, the distillation column reactor systems may be operated in a manner such that the nitrites are pushed down the column and exit with the heavier bottoms. Applicants have found that, depending upon the specific $C_2$ to $C_6$ alcohol or mixture of alcohols used and the azeotropes formed, nitrites may be pushed down the column by maintaining a selected alcohol concentration profile in the distillation column reactor system.

For example, Applicants have found that nitriles are at a high concentration at a lighter cut than the ethanol/amyl ether azeotrope. For etherification of mixtures containing primarily $C_5$s, nitrites may be pushed down the column by maintaining a selected ethanol concentration profile in the distillation column reactor system. Thus, to push nitrites down the column, and to minimize or avoid nitrites contacting the catalyst, ethanol may be maintained at a peak concentration at a point lower than the catalyst containing zone (or lower than the side draw fed to the catalyst containing reactor). In some embodiments, ethanol may be maintained at a peak concentration at a point lower than the feed location. In other embodiments, ethanol may be at a peak concentration in the bottoms. In yet other embodiments, the concentration of ethanol may increase from a top tray to a point lower than the catalyst containing zone (or lower than the side draw feeding the catalyst containing reactor). In other embodiments, the concentration of ethanol may increase from a top tray to a point lower than the feed location.

Similarly, other alcohol/hydrocarbon mixtures may be used in which a selected alcohol profile may minimize or avoid contact of nitrites with the catalyst. The selected alcohol profile may be limited, however, by the molecular weight of the reactants, alcohol and isoolefin, as a sufficient concentration of each is required in the catalyst zone to obtain the desired reaction.

In some embodiments, the etherification may be operated such that the etherification reaction zone is substantially free of propionitrile. Substantially free, as used herein, indicates that less than 25 percent of the propionitrile in the feed comes into contact with catalyst in the etherification reaction zone. In other embodiments, the etherification may be operated such that less than 2 ppm propionitrile in the feed contacts the etherification reaction zone; less than 1 ppm in other embodiments; less than 0.5 ppm in other embodiments; and less than 0.1 ppm in yet other embodiments. In some embodiments, the etherification may be operated such that propionitrile does not contact the etherification reaction zone at detectable concentrations.

Other Processes

Operation of a catalytic distillation reactor system as described above may be coupled with other systems. In some embodiments, the bottoms product from the distillation column may undergo subsequent separations, such as to recover the ether or any residual alcohol, for example. In other embodiments, the bottoms product including the ether may be used as a gasoline additive, such as where the concentration of nitrites and other nitrogen containing compounds in the bottoms product or gasoline blend is below the limits set for nitrogen-containing compounds in gasoline. In other embodiments, the overheads product from the distillation column may undergo subsequent separations, such as to recover any unreacted alcohol from the hydrocarbons. In various embodiments, alcohol and/or hydrocarbons recovered in any of these separation processes may be recycled to the distillation column reactor system for further processing.

In other embodiments, the feed may undergo processing steps prior to entry into the catalytic distillation reactor system. The above described systems for removing nitrites from hydrocarbon feedstocks, including washing, solvent extraction, use of guard beds, and other processes, may be used to remove at least a portion of the nitrites prior to feed of the hydrocarbon feedstock to the catalytic distillation reactor system. In this manner, operation of existing etherification processes may be improved according to embodiments disclosed herein, improving catalyst life and column operations, and the amount of nitrites entering the catalytic distillation system may be at least partially decreased.

In some embodiments, the hydrocarbon and alcohol feeds may be initially passed through a fixed-bed etherification reactor, converting at least a portion of the feed to ethers. The effluent from the reactor may then be forwarded to a catalytic distillation reactor system for further processing, where the catalytic distillation reactor system is operated in a manner to protect the etherification catalyst from nitrile contaminants, as described above. The fixed-bed reactor may be a single-phase reactor, such as a liquid or vapor phase reactor, a fixed-bed boiling point reactor, or a combination thereof.

In other embodiments, ethanol or additional ethanol may be added to the distillation column reactor system at a location above that of the hydrocarbon feed. For example, ethanol may be added to one or more of the top of the column, above the etherification catalyst zone, within the etherification catalyst zone, or to a tray below the etherification catalyst zone and above the feed tray. In this manner, the concentration of ethanol toward the top of the column may be increased, providing further driving force to maintain the catalyst substantially free of nitrile contaminants.

In yet other embodiments, column operations may be such that $C_6$ and heavier compounds in the feed preferentially traverse downward from the hydrocarbon feed location. Any upward travel of the $C_6$ and heavier compounds from the feed location may undesirably lift the propionitrile and other nitrile contaminants within the column toward the etherification catalyst zone.

EXAMPLES

Example 1

Oldershaw Distillation 1

Figure 3:
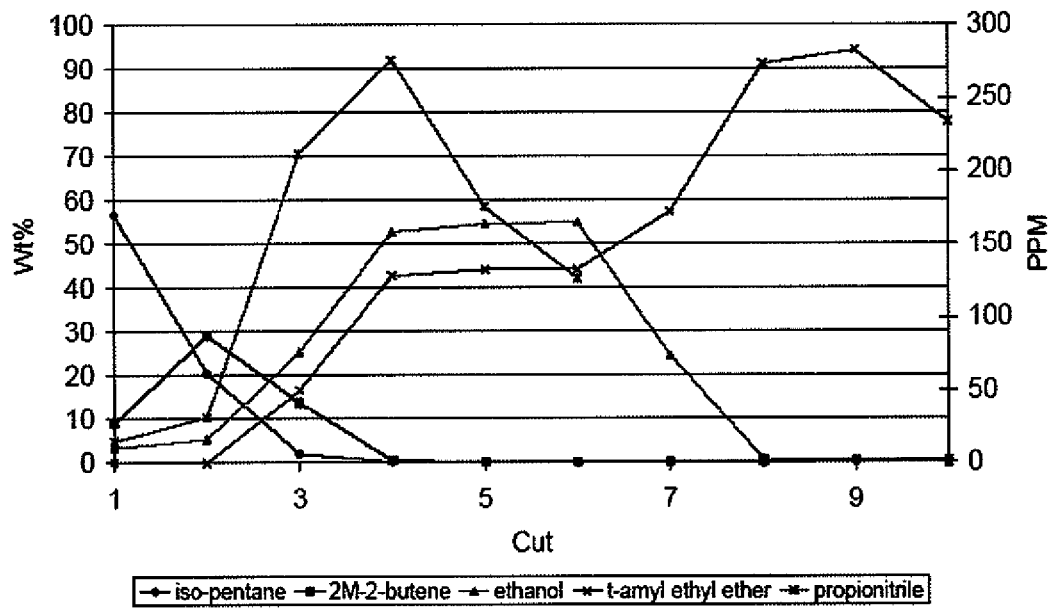
FIG. 3 presents results of an Oldershaw distillation for a mixture containing components that may be present in embodiments of an etherification process according to embodiments disclosed herein.

An Oldershaw distillation was performed on a mixture containing propionitrile in $C_5$s, ethanol and TAEE. The mixture included 25 weight percent $C_5$s, 25 weight percent ethanol, 50 weight percent TAEE, and 50 ppm propionitrile. The Oldershaw distillation was performed using a packed column at atmospheric pressure, taking 10 equal-volume cuts. The results of the distillation are illustrated in FIG. 3.

Example 2

Oldershaw Distillation 2

Figure 4:
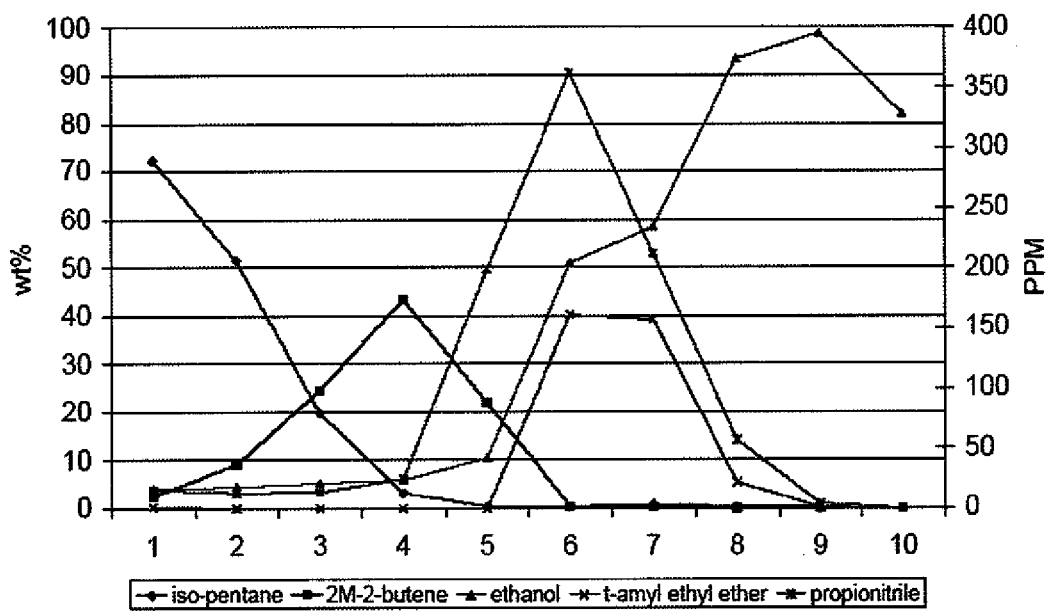
FIG. 4 presents results of an Oldershaw distillation for a mixture containing components that may be present in embodiments of an etherification process according to embodiments disclosed herein.

An Oldershaw distillation was performed on a mixture containing propionitrile in $C_5$s, ethanol and TAEE. The mixture included 50 weight percent $C_5$s, 40 weight percent ethanol, 10 weight percent TAEE, and 90 ppm propionitrile. The Oldershaw distillation was performed using a packed column at atmospheric pressure, taking 10 equal-volume cuts. The results of the distillation are illustrated in FIG. 4.

The results of the two Oldershaw distillations described above indicate that the highest concentration of propionitrile appeared just lighter than the ethanol/TAEE azeotrope. In Oldershaw Distillation 1, FIG. 3, the propionitrile concentration was greatest at cut 4, and is also present in cuts 1-3 and 5-6 to a lesser extent. In Oldershaw Distillation 2, FIG. 4, the propionitrile concentration was greatest at cut 6, with minimal concentration in cuts 1-4.

By comparison to prior art processes, such as described in U.S. Pat. Nos. 5,292,993 and 5,446,231, methanol azeotropic distillation has fundamentally different dynamics than the above described distillations using ethanol. In the methanol azeotropic distillation, propionitrile is pushed down the column. In contrast, the distillation using ethanol results in lifting the propionitrile to a point in the column above that of the ethanol/TAEE azeotrope. Thus, the ethanol concentration profile in the column may be an important variable in controlling the concentration profile of propionitrile in the column.

Example 3

Continuous Catalytic Distillation

A catalytic distillation reactor was used to demonstrate the production of TAEE with FCC $C_5$s and ethanol. The feed was a mixture of primarily C5 paraffins and olefins from FCC naphtha, to which ethanol was added, containing 17 wt % isoamylenes (IA), a small amount of $C_6$ compounds (up to a few weight percent) and about 20 ppm propionitrile. The column was 110 feet high, with catalyst located between 60 feet and 100 feet, and the feed point was located at 45 feet. The feed containing isoamylenes was fed to a fixed bed boiling point reactor. The reactor effluent then proceeded to the stripping section of a catalytic distillation column. The fixed bed reactor contained about 42 lbs. of Rohm and Haas A35 etherification catalyst. The catalytic distillation column contained 36 feet of CDModules (a proprietary structured packing available from Catalytic Distillation Technologies) containing Rohm and Haas A35 etherification catalyst. The remaining 44 feet of the catalytic distillation column contained ⅝ inch Pall rings. Inlet temperature to the primary reactor was 120° F. The catalytic distillation column was operated between 40 and 60 psig. Feed flow was varied from 0 to 110 lb/hr. Reflux was varied from 100 to 200 lb/hr. Overall isoamylene conversion was between 65 and 98%. The ethanol-to-isoamylene molar ratio was varied from 1 to 2.5+During the operation of the column, liquid samples were taken at various column heights.

Figure 5:
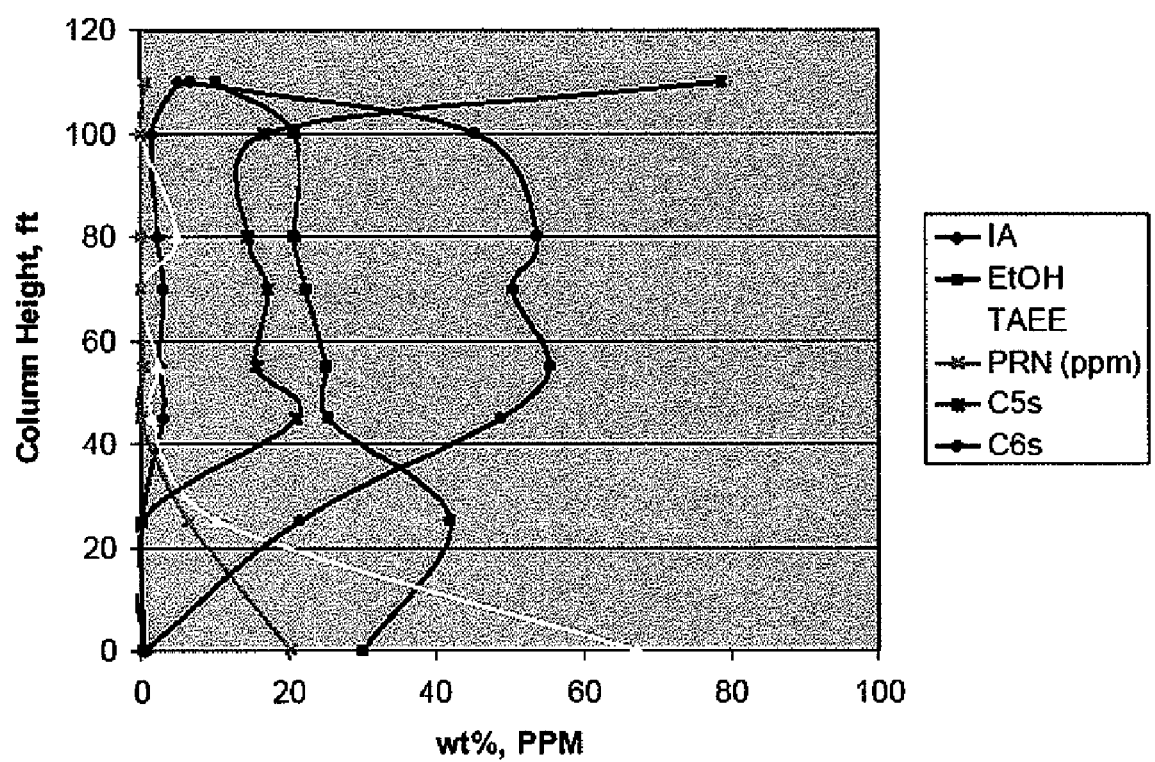
FIG. 5 presents operating results of an etherification process according to embodiments disclosed herein.

A snapshot of the Continuous Catalytic Distillation operations is presented in FIG. 5, illustrating conditions after 141 hours of continuous operation. As illustrated in FIG. 5, maintaining an ethanol profile such that the ethanol concentration is greatest below the feed point results in the propionitrile exiting the bottom of the column. Additionally, the propionitrile concentration is substantially negligible above the feed location. The negligible concentration of propionitrile above the feed location may be attributed to the increasing concentration of ethanol from the top of the column to a point below the feed location, helping to pull the propionitrile toward the bottom of the column.

Additional observations made during column operations (Example 3) indicated that a secondary ethanol injection in the column, above the feed location, may be beneficial to directing the propionitrile downward in the column. This increases the concentration of ethanol in the top portion of the column, further driving the propionitrile in the desired direction within the column. Additionally, it is beneficial to operate the column such that $C_6$ and heavier compounds in the feed are directed more downward than upwards in the column, thus minimizing the "lift" that propionitrile in the feed may encounter.

Advantageously, embodiments disclosed herein may provide for an etherification process that may minimize or eliminate contact of propionitrile with an etherification catalyst by maintaining a selected alcohol concentration profile in the distillation column reactor system. Applicant's have discovered that, contrary to the prior art, ethanol may be used in etherification reactions and propionitrile may be pushed toward the bottom of the column, thus negating or lessening the need for feed pre-treatment to remove or react nitrites from the hydrocarbon feed mixture. By maintaining a selected alcohol concentration profile in the distillation column reactor, it may be possible to minimize piece count, due to the decreased need for feed pre-treatment and other separation processes, which may simplify the etherification process and decrease capital and operating cost.

Additionally, as it has been shown in the prior art that propionitrile or other contaminants may pass through guard beds and water washing, embodiments disclosed herein may be used to improve existing processes, advantageously minimizing contact of the remaining contaminants after pre-treatment, including propionitrile, with etherification catalysts. For example, whereas existing processes may have been limited to production of methyl ethers, by operating at a selected alcohol concentration profile, existing processes may now be able to produce ethyl ethers without significant deactivation of the etherification catalyst due to propionitrile.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of tertiary ethers, the process comprising:
    feeding a hydrocarbon steam comprising isoolefins and propionitrile to a distillation column reactor system containing at least one etherification reaction zone containing an etherification catalyst;
    feeding a $C_2$ to $C_6$ monoalcohol or mixture thereof to the distillation column reactor system;
    concurrently in the distillation column reactor system:
        reacting a portion of the isoolefins with a portion of the alcohols to form a tertiary ether; and
        separating the tertiary ether from unreacted isoolefins;
    withdrawing the tertiary ether and propionitrile from the distillation column reactor system as a bottoms;
    withdrawing the unreacted isoolefins from the distillation column reactor system as an overheads; and
    operating the distillation column reactor system such that the etherification reaction zone is substantially free of propionitrile.

2. The process of claim 1, wherein the hydrocarbon stream is fed to the distillation column reactor at a point below the etherification reaction zone.

3. The process of claim 1, wherein the operating comprises operating the distillation column reactor system such that less than 2 ppm propionitrile in the hydrocarbon steam contacts the etherification reaction zone.

4. The process of claim 1, wherein the operating comprises operating the distillation column reactor system such that less than 1 ppm propionitrile in the hydrocarbon stream contacts the etherification reaction zone.

5. The process of claim 1, wherein the operating comprises operating the distillation column reactor system such that propionitrile does not contact the etherification reaction zone at detectible concentrations.

6. The process of claim 1, wherein the distillation column reactor system comprises a distillation column having a liquid side draw feeding an etherification reactor, wherein the product from the etherification reactor is returned to the distillation column.

7. The process of claim 1, wherein the operating comprises maintaining a concentration of alcohol at a maximum at a location between the etherification reaction zone and the bottoms.

8. The process of claim 7 wherein the operating further comprises maintaining a decreasing concentration of alcohol from the location of maximum concentration to the overheads of the column.

9. The process of claim 1, wherein the hydrocarbon stream comprises $C_4$ to $C_7$ hydrocarbons from an FCC unit.

10. The process of claim 9, wherein the hydrocarbon stream comprises $C_5$ to $C_6$ hydrocarbons from an FCC unit.

11. The process of claim 1, wherein the hydrocarbon stream comprises at least 5 ppm propionitrile.

12. The process of claim 11, wherein the hydrocarbon stream comprises at least 20 ppm propionitrile.

13. The process of claim 1, wherein the bottoms further comprise unreacted alcohol, the process further comprising separating the alcohol and the ether.

14. The process of claim 1, further comprising adding ethanol to the column at a point above a hydrocarbon feed point.

15. The process of claim 1, further comprising
    reacting a mixture comprising isoamylenes and ethanol in a fixed bed reactor;
    recovering an effluent from the fixed bed reactor effluent for use as the hydrocarbon stream comprising isoolefins and propionitrile.

16. A process for the production of tertiary amyl ethyl ether, the process comprising:
    feeding a hydrocarbon stream comprising $C_5$ isoolefins and propionitrile to a distillation column reactor containing at least one etherification distillation reaction zone containing an etherification catalyst, wherein the stream comprising the hydrocarbons is fed to the distillation column reactor at a point below the etherification distillation reaction zone;
    feeding ethanol to the distillation column reactor;
    concurrently in the distillation column reactor:
        reacting a portion of the $C_5$ isoolefins with a portion of the ethanol to form tertiary amyl ethyl ether; and
        separating the tertiary amyl ethyl ether from unreacted $C_5$ isoolefins;
    withdrawing the tertiary amyl ethyl ether and propionitrile from the distillation column reactor as a bottoms;
    withdrawing the unreacted $C_5$ isoolefins from the distillation column reactor as an overheads; and
    operating the distillation column reactor such that the etherification distillation reaction zone is substantially free of propionitrile.

17. The process of claim 16, wherein the hydrocarbon stream comprises at least 5 ppm propionitrile.

18. The process of claim 17, wherein the operating comprises operating the distillation column reactor such that less than 1 ppm propionitrile in the hydrocarbon stream contacts the etherification distillation reaction zone.

19. The process of claim 18, wherein the operating comprises operating the distillation column reactor such that propionitrile does not contact the etherification reaction zone at detectible concentrations.

20. The process of claim 16, wherein the operating comprises maintaining a concentration of ethanol at a maximum at a location between the etherification distillation reaction zone and the bottoms.

21. The process of claim 20, wherein the operating further comprises maintaining a decreasing concentration of ethanol from the location of maximum concentration to the overheads of the column.

22. The process of claim 16, wherein the bottoms further comprise unreacted ethanol, the process further comprising separating the ethanol from the tertiary amyl ethyl ether.

23. The process of claim 16, further comprising adding ethanol to the column at a point above a hydrocarbon feed point.

24. The process of claim 16, further comprising
    reacting a mixture comprising isoamylenes and ethanol in a fixed bed reactor;
    recovering an effluent from the fixed bed reactor for use as the hydrocarbon stream comprising isoolefins and propionitrile.

* * * * *